United States Patent
Kang et al.

(10) Patent No.: US 11,414,364 B2
(45) Date of Patent: Aug. 16, 2022

(54) METHOD FOR DECOMPOSING PHENOLIC BY-PRODUCTS

(71) Applicant: LG CHEM, LTD, Seoul (KR)

(72) Inventors: Min Suk Kang, Daejeon (KR); Sang Beom Lee, Daejeon (KR); Chi Hyun Jang, Daejeon (KR)

(73) Assignee: LG Chern, Ltd., Seoul (KR)

( * ) Notice: Subject to any disclaimer, the term of this patent is extended or adjusted under 35 U.S.C. 154(b) by 0 days.

(21) Appl. No.: 17/422,686

(22) PCT Filed: Aug. 11, 2020

(86) PCT No.: PCT/KR2020/010601
§ 371 (c)(1),
(2) Date: Jul. 13, 2021

(87) PCT Pub. No.: WO2021/054608
PCT Pub. Date: Mar. 25, 2021

(65) Prior Publication Data
US 2022/0106241 A1    Apr. 7, 2022

(30) Foreign Application Priority Data
Sep. 16, 2019 (KR) .................. 10-2019-0113589

(51) Int. Cl.
*C07C 7/04* (2006.01)
*C07C 37/74* (2006.01)
*C07C 45/82* (2006.01)
*B01D 17/00* (2006.01)
*B01D 17/02* (2006.01)

(52) U.S. Cl.
CPC ............... *C07C 7/04* (2013.01); *B01D 17/02* (2013.01); *C07C 37/74* (2013.01); *C07C 45/82* (2013.01)

(58) Field of Classification Search
CPC ........... C07C 7/04; C07C 37/74; C07C 45/82; B01D 17/00
See application file for complete search history.

(56) References Cited

U.S. PATENT DOCUMENTS 4,158,611 A    6/1979    Cooke

FOREIGN PATENT DOCUMENTS

| CN | 102992961 A | 3/2013 |
|---|---|---|
| CN | 109422613 A | 3/2019 |
| JP | 5-117184 A | 5/1993 |
| JP | 2001-2611 A | 1/2001 |
| KR | 91-1098 B1 | 2/1991 |
| KR | 10-0396718 B1 | 12/2003 |
| KR | 10-2011-0081873 A | 7/2011 |
| KR | 10-2017-0047030 A | 5/2017 |
| KR | 10-2019-0058273 A | 5/2019 |
| WO | 00/40531 A1 | 7/2000 |

*Primary Examiner* — Sikarl A Witherspoon
(74) *Attorney, Agent, or Firm* — Dentons US LLP

(57) ABSTRACT

The present disclosure provides a method for decomposing a phenolic by-product, the method including: a step S10 of feeding a phenolic by-product stream to a decomposition apparatus and thermally cracking the phenolic by-product stream; a step S20 of recovering an active ingredient from a top discharge stream of the decomposition apparatus and discharging a substance having a high boiling point through a bottom discharge stream of the decomposition apparatus; a step S30 of passing a part of the bottom discharge stream of the decomposition apparatus through a reboiler and then feeding the part of the bottom discharge stream of the decomposition apparatus to the decomposition apparatus and discharging a residual stream of the bottom discharge stream of the decomposition apparatus; and a step S40 of feeding a side discharge stream of the decomposition apparatus to the reboiler.

10 Claims, 2 Drawing Sheets

(a) (b) (c)

METHOD FOR DECOMPOSING PHENOLIC BY-PRODUCTS

CROSS-REFERENCE TO RELATED APPLICATIONS

The present application is a National Phase entry pursuant to 35 U.S.C. § 371 of International Application No. PCT/KR2020/010601, filed on Aug. 11, 2020, and claims the benefit of and priority to Korean Patent Application No. 10-2019-0113589, filed on Sep. 16, 2019, the disclosures of which are incorporated by reference in their entirety for all purposes as if fully set forth herein.

TECHNICAL FIELD

The present invention relates to a method for decomposing a phenolic by-product, and more particularly, to a method of removing a contaminant accumulated in a reboiler when decomposing a phenolic by-product produced in a phenol production process.

BACKGROUND ART

In general, about 95% of phenol used in the world is produced by a Hock process. The Hock process is performed in three steps including: a step (1) of forming cumene by alkylation of benzene with propylene, a step (2) of oxidizing the cumene to cumene hydroperoxide (CHP) by combining the cumene and oxygen, and a step (3) of decomposing the cumene hydroperoxide into phenol and acetone by an acid decomposition reaction in the presence of an acid catalyst.

Here, in the cumene oxidation step which is the step (2), by-products such as acetophenone (AP), dimethyl benzyl alcohol (DMBA), dicumylperoxide (DCP), and dicumene (DC) are produced in addition to cumene hydroperoxide.

In addition, in the acid decomposition reaction of the cumene hydroperoxide in the step (3), by-products such as hydroxy acetone (HA), 2-methylbenzofuran (2-MBF), alpha-methyl styrene (AMS), mesityl oxide (MO), alpha-methyl styrene (AMS) dimer, and cumylphenol (CP) are produced in addition to phenol and acetone.

Accordingly, since a product stream produced in such a reaction process is present in a state in which phenol, acetone, and various by-products are mixed with each other, a separation process for separating the phenol from the product stream is required.

The product stream is injected into a separate separation apparatus, an acetone-based mixture including unreacted cumene, acetone, alpha-methyl styrene, hydroxy acetone, and the like is separated through a top of the separation apparatus, and a phenolic mixture including phenol, a part of alpha-methyl styrene, 2-methylbenzofuran, and other by-products is separated through a bottom of the separation apparatus.

The phenolic mixture separated through the bottom of the separation apparatus is injected into a phenol column, phenol is separated through a top of the phenol column, and phenolic by-products such as dicumylperoxide, cumylphenol, alpha-methyl styrene dimer, and tar are separated through a bottom of the phenol column.

Meanwhile, in the related art, the phenolic by-product separated through the bottom of the phenol column is used as fuel or discarded without an additional treatment. However, since the phenolic by-product separated through the bottom of the phenol column includes phenol which is a product, some active ingredients such as alpha-methyl styrene, in addition to tar that is an impurity, the active ingredients are required to be separated and recovered from the phenolic by-product. In addition, in case of decomposing by-products included in the phenolic by-product, it is possible to produce cumene and the like.

Accordingly, studies for obtaining phenol and an active ingredient that remain in the phenolic by-product separated through the bottom of the phenol column, and phenol and an active ingredient that are produced by decomposition of the phenolic by-product have been conducted.

DISCLOSURE

Technical Problem

In order to solve the problems mentioned in the background art, an object of the present invention is to provide a method of effectively removing a contaminant accumulated in a reboiler while obtaining an active ingredient by decomposing a phenolic by-product produced in a phenol production process.

That is, an object of the present invention is to provide a method of effectively removing a contaminant accumulated in a reboiler provided below a decomposition apparatus due to a substance having a high boiling point generated in a phenolic by-product decomposition process, while effectively obtaining an active ingredient by decomposing a phenolic by-product.

Technical Solution

In one general aspect, a method for decomposing a phenolic by-product includes: a step S10 of feeding a phenolic by-product stream to a decomposition apparatus and thermally cracking the phenolic by-product stream; a S20 of recovering an active ingredient from a top discharge stream of the decomposition apparatus and discharging a substance having a high boiling point through a bottom discharge stream of the decomposition apparatus; a step S30 of passing a part of the bottom discharge stream of the decomposition apparatus through a reboiler and then feeding the part of the bottom discharge stream of the decomposition apparatus to the decomposition apparatus and discharging a residual stream of the bottom discharge stream of the decomposition apparatus; and a step S40 of feeding a side discharge stream of the decomposition apparatus to the reboiler.

Advantageous Effects

In a case where the phenolic by-product produced in the phenol production process is decomposed according to the method for decomposing a phenolic by-product according to the present invention, a content of the acetophenone in the active ingredient can be reduced while effectively obtaining the active ingredient by decomposing the phenolic by-product.

Further, in a case where the phenolic by-product produced in the phenol production process is decomposed according to the method for decomposing a phenolic by-product according to the present invention, it is possible to prevent cost-effectiveness problems caused by an increase in dismantling and disassembling operation time due to a contaminant adhering to the inside of the reboiler in a solid state and shut-down for a certain period due to an increase in operation time to remove the contaminant during the cleaning of the inside of the reboiler. In addition, cleaning efficiency can be improved and an operation cost can be reduced by using a recovered stream having a high temperature.

BEST MODE

Figure 1:
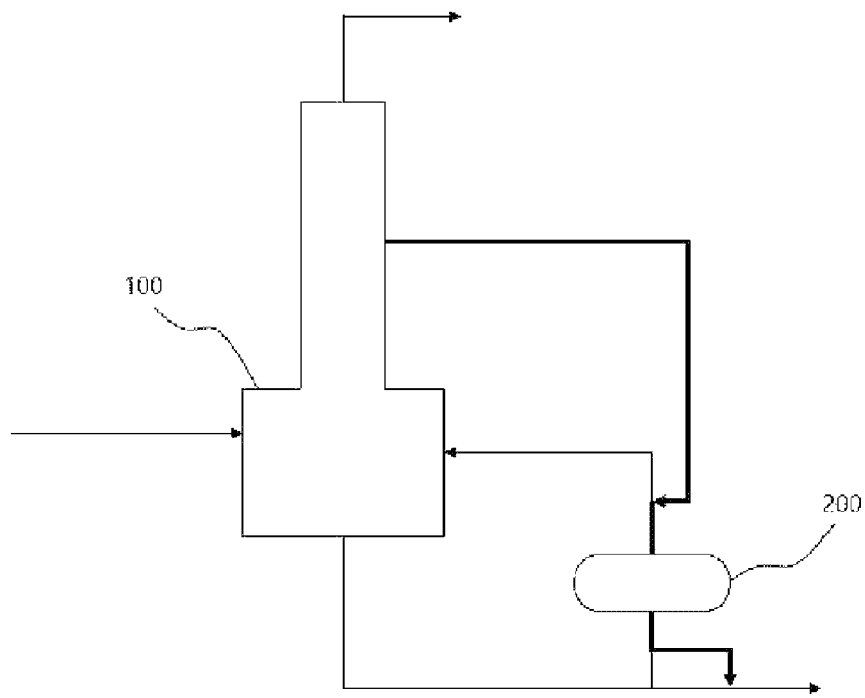
FIG. 1 is a process flow diagram of a method for decomposing a phenolic by-product according to an exemplary embodiment of the present invention.

The terms and words used in the description and claims of the present invention are not to be construed as general or dictionary meanings but are to be construed as meanings and concepts meeting the technical ideas of the present invention based on a principle that the inventors can appropriately define the concepts of terms in order to describe their own inventions in best mode.

The term "stream" in the present invention may refer to a flow of a fluid in a process, and may also refer to a fluid flowing through a pipe itself. Specifically, the "stream" may refer to both the fluid flowing through the pipe connecting respective apparatuses to each other itself and the flow of the fluid at the same time. In addition, the fluid may refer to gas.

Hereinafter, the present invention will be described in more detail with reference to FIG. 1 in order to assist in the understanding of the present invention.

A method for decomposing a phenolic by-product according to the present invention can be a method for decomposing a phenolic by-product produced in a phenol production process. According to an exemplary embodiment of the present invention, the phenol production process can be a Hock process.

According to an exemplary embodiment of the present invention, the method for decomposing a phenolic by-product can include: a step S10 of feeding a phenolic by-product stream to a decomposition apparatus 100 and thermally cracking the phenolic by-product; a step S20 of recovering an active ingredient from a top discharge stream of the decomposition apparatus 100 and discharging a substance having a high boiling point through a bottom discharge stream of the decomposition apparatus 100; a step S30 of passing a part of the bottom discharge stream of the decomposition apparatus 100 through a reboiler 200 and then feeding the part of the bottom discharge stream of the decomposition apparatus 100 to the decomposition apparatus and discharging a residual stream of the bottom discharge stream of the decomposition apparatus 100; and a step S40 of feeding a side discharge stream of the decomposition apparatus 100 to the reboiler 200.

According to an exemplary embodiment of the present invention, the phenolic by-product fed to the decomposition apparatus 100 can be fed to the decomposition apparatus 100 after removing a salt.

Specifically, the phenol production process can be performed by including the acid decomposition reaction of cumene hydroperoxide described above. In this case, since the acid decomposition reaction of the cumene hydroperoxide is performed by including acid, an acid decomposition reaction solution contains acid. Therefore, in order to obtain phenol and acetone from the acid decomposition reaction solution through a process such as distillation, it is required to perform a process of neutralizing the acid decomposition reaction solution.

Prior to separation of the acid decomposition reaction solution, the acid decomposition reaction solution is neutralized by a basic aqueous solution or the like. In this case, in the neutralized acid decomposition reaction solution, a salt is generated by a neutralization reaction between the acid used in the acid decomposition reaction and the base in the basic aqueous solution or the like. A phase of the acid decomposition reaction solution neutralized by the neutralization process is separated into an oil phase and a liquid phase. A separation process for obtaining phenol and acetone from the separated oil phase is performed. In this case, the salt is mostly removed together with the liquid phase, but a part of the salt remains in the oil phase.

After a separation process of phenol, the salt finally remains in a phenolic by-product described in the present invention. The salt remaining in the phenolic by-product causes corrosion, occlusion, and deposition in the decomposition apparatus 100 when the phenolic by-product is decomposed to obtain the active ingredient from the phenolic by-product later, which causes a breakdown in the decomposition apparatus 100. Therefore, it is important to minimize the salt included in the phenolic by-product when decomposing the phenolic by-product.

Accordingly, the salt included in the phenolic by-product can be removed by any one of the following methods: a method of removing the salt by injecting process water prior to the decomposition of the phenolic by-product; a method of removing the salt by injecting, to the phenolic by-product, organic matters such as cumene and alpha-methyl styrene discharged as active ingredients from an acetone column or the like in the phenol production process together with process water; a method of removing the salt by injecting, to the phenolic by-product, organic matters such as phenol, cumene, and alpha-methyl styrene discharged as active ingredients through the top discharge stream of the decomposition apparatus 100 which decomposes the phenolic by-product together with process water; and a method of removing the salt by injecting, to the phenolic by-product, organic matters such as acetophenone, phenol, alpha-methyl styrene, and cumene from the side discharge stream of the decomposition apparatus 100 which decomposes the phenolic by-product together with process water. Among them, the method of removing the salt by injecting, to the phenolic by-product, organic matters such as acetophenone, phenol, alpha-methyl styrene, and cumene from the side discharge stream of the decomposition apparatus 100 which decomposes the phenolic by-product together with process water can be most preferable in consideration of a reduction in load and energy of the apparatus.

After the salt is removed from the phenolic by-product stream, a phase of the phenolic by-product stream can be separated into a liquid phase and an oil phase. The liquid phase can be discharged, and the oil phase can be fed to the decomposition apparatus 100 which decomposes the phenolic by-product as a phenolic by-product stream from which the salt is removed.

According to an exemplary embodiment of the present invention, the phenolic by-product stream can include one or more selected from the group consisting of phenol, alpha-methyl styrene, acetophenone, cumylphenol, and alpha-methyl styrene dimer. As a specific example, the phenolic by-product stream can include two or more selected from the group consisting of phenol, alpha-methyl styrene, acetophenone, cumylphenol, and alpha-methyl styrene dimer, or all of them. These components can be components included in the phenolic by-product discharged in the process of separating the acetone-based mixture and the phenolic mixture from the acid decomposition reaction solution in the phenol production process by the separation apparatus and separating the phenol and the phenolic by-product from the phenolic mixture by the phenol column.

According to an exemplary embodiment of the present invention, the decomposition performed in the decomposition apparatus 100 can be thermal cracking, and the decomposition apparatus 100 for performing this can be a thermal cracker. As a specific example, the thermal cracker can be a reactor-distillation tower integrated type separation apparatus.

According to an exemplary embodiment of the present invention, the decomposition in the step S10 can be performed by intentionally lowering a temperature below an operation temperature for obtaining the entire amount of the phenol from the top discharge stream of the decomposition apparatus 100 to discharge the acetophenone through the side discharge stream of the decomposition apparatus as much as possible. Specifically, since a difference in boiling point between the phenol (boiling point: 181.7° C.) and the acetophenone (boiling point: 202° C.) is small and the phenol forms an azeotrope with the acetophenone, in a case where an operation temperature of the decomposition apparatus 100 is increased to obtain the phenol from a top of the decomposition apparatus 100 as much as possible, a part of the acetophenone can be included in the active ingredient together with the phenol and discharged.

As a specific example, the operation temperature of the decomposition apparatus 100 in the step S10 can be 260° C. to 600° C., 290° C. to 500° C., or 300° C. to 350° C. Within these ranges, the acetophenone is discharged through the side discharge stream of the decomposition apparatus 100 as much as possible, which is effective in minimizing a content of the acetophenone in the top discharge stream of the decomposition apparatus 100.

In addition, according to an exemplary embodiment of the present invention, in the step S10, the decomposition apparatus 100 can be operated at a pressure of 0.1 bar to 3.0 bar, 0.1 bar to 2.0 bar, or 0.1 bar to 1.5 bar in order to separate the components in the side discharge stream of the decomposition apparatus 100 and the top discharge stream of the decomposition apparatus 100. In this case, the operation temperature of the decomposition apparatus 100 can be kept at a low temperature, and dimerization or polymerization of the alpha-methyl styrene in the active ingredients included in the top discharge stream of the decomposition apparatus 100 can be prevented. In addition, the operation temperature can be kept at a low temperature, such that the thermal energy required for the operation of the decomposition apparatus 100 can be reduced.

According to an exemplary embodiment of the present invention, the decomposition apparatus 100 can be a multi-stage decomposition apparatus. In this case, the side discharge stream of the decomposition apparatus 100 can be discharged at a middle position (corresponding to 25% to 90%, 40% to 90%, or 50% to 90% of the total stages) of a side of the decomposition apparatus. In this case, the amount of the acetophenone discharged through the top discharge stream of the decomposition apparatus 100 can be significantly reduced.

According to an exemplary embodiment of the present invention, in the step S20, the active ingredients can be recovered through the top discharge stream of the decomposition apparatus 100, and a substance having a high boiling point can be discharged through the bottom discharge stream of the decomposition apparatus 100.

The top discharge stream of the decomposition apparatus 100 can include one or more selected from the group consisting of phenol, alpha-methyl styrene, and cumene, as the active ingredients. The active ingredient can include the phenol which is not separated at the bottom of the phenol column and is included in the phenolic by-product stream and the phenol which is decomposed in the phenolic by-product decomposition step S10 and is discharged through the top discharge stream of the decomposition apparatus 100. In addition, the active ingredient can include useful components which can be additionally used (for example, alpha-methyl styrene, cumene, and the like) and useful components which are decomposed in the phenolic by-product decomposition step S10 and discharged through the top discharge stream of the decomposition apparatus in addition to the phenol, among the components separated at the bottom of the phenol column and included in the phenolic by-product stream. That is, the active ingredient can refer to a component decomposed in the phenolic by-product decomposition step S10 and discharged through the top discharge stream of the decomposition apparatus.

The bottom discharge stream of the decomposition apparatus 100 can include a substance having a high boiling point that is generated in the decomposition process of the phenolic by-product due to thermal cracking at a high temperature during the thermal cracking of the phenolic by-product. For example, the substance having the high boiling point can include tar. The tar can include tar which is separated at the bottom of the phenol column and is included in the phenolic by-product stream and tar which is decomposed in the phenolic by-product decomposition step S10 and is discharged through the bottom discharge stream of the decomposition apparatus 100.

A part of the bottom discharge stream of the decomposition apparatus 100 is passed through the reboiler 200 and then fed to the decomposition apparatus 100, and a residual stream of the bottom discharge stream of the decomposition apparatus 100 can be discharged. In this case, one or two or more reboilers 200 can be installed. For example, when two reboilers 200 are installed, the part of the bottom discharge stream of the decomposition apparatus 100 can be passed through a first reboiler and then fed to the decomposition apparatus 100, a part of the residual stream can be passed through a second reboiler and then fed to the decomposition apparatus 100, and a remaining residual stream of the bottom discharge stream of the decomposition apparatus 100 can be discharged.

The part of the bottom discharge stream of the decomposition apparatus 100 can be fed to the reboiler 200 and reheated. The reheated stream can be discharged from the reboiler 200 and fed to the decomposition apparatus 100. By doing so, the active ingredient in the bottom discharge stream of the decomposition apparatus 100 can be reduced as much as possible other than tar which is an impurity.

In such a process, a part of the tar included in the bottom discharge stream of the decomposition apparatus 100 fed to the reboiler 200 is accumulated in the reboiler 200, which causes fouling in the reboiler 200. In the related art, in a case where the tar is accumulated in the reboiler 200 in a certain amount or more, it is difficult to operate the decomposition apparatus 100, and thus, an operation of each of the decomposition apparatus 100 and the reboiler 200 is shut down, the decomposition apparatus 100 and the reboiler 200 are disassembled, and the inside of the reboiler 200 is cleaned. Accordingly, it takes a long time to clean the reboiler 200 due to the time it takes to disassemble the decomposition apparatus 100 and the reboiler 200. Therefore, a shut down time of the decomposition apparatus 100 is increased, which leads to an economical loss and an increase in cost of the active ingredient.

On the other hand, in the method for decomposing a phenolic by-product according to the present invention, the side discharge stream of the decomposition apparatus 100 is used to clean the reboiler 200, such that the decomposition apparatus 100 and the reboiler 200 are not required to be disassembled as a cleaning method of the reboiler 200 according to the related art, and the organic matter in the side discharge stream of the decomposition apparatus 100 having a high temperature is used as a solvent to dissolve the contaminant accumulated in the reboiler 200, thereby more easily performing the cleaning.

According to an exemplary embodiment of the present invention, the side discharge stream of the decomposition apparatus 100 is a stream discharged from the side of the decomposition apparatus 100, and can include one or more selected from the group consisting of phenol, acetophenone, alpha-methyl styrene, and cumene. As a specific example, the side discharge stream of the decomposition apparatus can include phenol, acetophenone, alpha-methyl styrene, and cumene. The reason why the side discharge stream of the decomposition apparatus 100 is injected into the reboiler 200 is to allow the organic matter included in the side discharge stream of the decomposition apparatus 100 to have an appropriate composition, temperature, and the like that allows the contaminant accumulated in the reboiler 200 to dissolve, thereby effectively dissolving and removing the contaminant accumulated on an inner wall and a pipe of the reboiler 200.

The acetophenone can be included in the side discharge stream of the decomposition apparatus 100 in an amount of 50 wt % or more. For example, the acetophenone can be included in the side discharge stream of the decomposition apparatus 100 in an amount of 50 wt % to 99 wt %, 55 wt % to 99 wt %, or 60 wt % to 99 wt %. The acetophenone is an organic matter included in the phenolic by-product stream, and acts as an impurity in contrast to the active ingredient obtained by the phenolic by-product decomposition reaction. Accordingly, it is preferable that a content of the acetophenone in the active ingredient is minimized. Therefore, when the acetophenone is included in the side discharge stream of the decomposition apparatus 100 in an amount of 50 wt % or more according to the present invention, the contaminant accumulated in the reboiler 200 can be effectively removed in a short time in the step S40 of feeding the side discharge stream of the decomposition apparatus 100 to the reboiler 200, and the content of the acetophenone in the active ingredient obtained by the phenolic by-product decomposition reaction can be minimized, which is advantageous in obtaining the active ingredient.

A temperature of the side discharge stream of the decomposition apparatus 100 can be 150° C. to 500° C. For example, the temperature of the side discharge stream of the decomposition apparatus 100 can be 160° C. to 400° C., 170° C. to 400° C., or 170° C. to 250° C. The side discharge stream of the decomposition apparatus 100 is affected by the operation temperature of the decomposition apparatus 100 and is discharged at a high temperature. The side discharge stream of the decomposition apparatus 100 having the high temperature of the above range is fed to the reboiler 200 and acts as steam having a high temperature to effectively dissolve the contaminant.

According to an exemplary embodiment of the present invention, the step S40 of feeding the side discharge stream of the decomposition apparatus 100 to the reboiler 200 can be performed in a case where the contaminant is accumulated in the reboiler 200 in a certain amount or more and an operation capability of the reboiler 200 is thus reduced to 85% or less. For example, the step S40 can be performed in a case where the operation capability of the reboiler 200 is 60% to 85%, 65% to 85%, or 70% to 85%. When the operation capability of the reboiler 200 is in the above ranges, there is no problem in the operation of the reboiler 200, but a function for reheating the bottom discharge stream of the decomposition apparatus 100 can be slightly deteriorated. The side discharge stream of the decomposition apparatus 100 is fed to the reboiler 200 having the operation capability of the above range to dissolve the contaminant accumulated in the reboiler 200, such that the operation capability of the reboiler 200 can be improved. Therefore, the problems caused by the cleaning method of the reboiler 200 according to the related art are resolved and the step S40 is performed, such that process energy can be further saved.

According to an exemplary embodiment of the present invention, in the step S40 of feeding the side discharge stream of the decomposition apparatus 100 to the reboiler 200, the side discharge stream of the decomposition apparatus 100 having a high temperature is fed to the reboiler 200 in a state where connection between the bottom discharge stream of the decomposition apparatus 100 and the reboiler 200 is blocked using a device such as a valve to dissolve and remove the contaminant accumulated in the reboiler 200. Specifically, in a case where the contaminant is accumulated in the reboiler 200 in a certain amount or more, the operation capability of the reboiler 200 can be slightly deteriorated, and in only this case, the side discharge stream of the decomposition apparatus 100 having a high temperature is fed to the reboiler 200 to remove the contaminant in a short time. The bottom discharge stream of the decomposition apparatus 100 and the reboiler 200 are connected to each other again using the valve, such that the operation can be restarted by a simple method. In this case, the cleaning time can be significantly reduced as compared with the cleaning method of the reboiler 200 according to the related art.

According to an exemplary embodiment of the present invention, a flow rate of the side discharge stream of the decomposition apparatus 100 fed to the reboiler 200 can be 0.05 to 0.6 of a flow rate of the phenolic by-product stream. For example, the flow rate of the side discharge stream of the decomposition apparatus 100 fed to the reboiler 200 can be 0.08 to 0.58, 0.1 to 0.55, or 0.1 to 0.53 of the flow rate of the phenolic by-product stream. The side discharge stream of the decomposition apparatus 100 is fed at the flow rate of the above range, such that the contaminant cleaning efficiency of the reboiler 200 can be improved while minimizing the process cost.

Hereinabove, the method for decomposing a phenolic by-product according to the present invention has been described and illustrated in the drawing. However, the description and the illustration of the drawing are for only essential components for understanding the present invention, and processes and apparatuses not separately described and illustrated can be properly applicable and used for implementing the method for decomposing a phenolic by-product, in addition to the processes and apparatuses described and illustrated in the drawing.

Hereinafter, the present invention will be described in more detail by examples. However, the following examples are provided for illustrating the present invention. It is apparent to a person skilled in the art that various modifications and alterations may be made without departing from the scope and spirit of the present invention, and the scope of the present invention is not limited thereto.

EXAMPLES

Example 1

As a process flow diagram illustrated in FIG. 1, a phenolic by-product stream of a composition shown in Table 1 was fed to a decomposition apparatus 100 at a flow rate of 1,000 kg/hr and the phenolic by-product stream was thermally cracked. In this case, an operation pressure of the decomposition apparatus 100 was controlled to normal pressure and an operation temperature of the decomposition apparatus 100 was controlled to 330° C. Active ingredients of compositions shown in Table 2 were recovered from a top discharge stream of the decomposition apparatus 100. A part of a bottom discharge stream of the decomposition apparatus 100 was fed to a reboiler 200 and a residual stream was discharged. In this case, a side discharge stream of the decomposition apparatus 100 was fed to the reboiler 200 at a flow rate of 300 kg/hr to remove a contaminant accumulated in the reboiler 200 (solid line). Compositions of the side discharge stream of the decomposition apparatus 100 are shown in Table 1.

TABLE 1

| Classification | | Phenolic by-product stream | Side discharge stream of decomposition apparatus |
|---|---|---|---|
| Phenol | (wt %) | 4.13 | 28.25 |
| Alpha-methyl styrene | (wt %) | 7.73 | 8.64 |
| Cumene | (wt %) | 0.00 | 1.07 |
| Acetophenone | (wt %) | 18.84 | 62.01 |
| Cumylphenol | (wt %) | 27.49 | 0.00 |
| Alpha-methyl styrene dimer | (wt %) | 15.10 | 0.00 |
| Etc. | (wt %) | 26.71 | 0.03 |
| Total | (wt %) | 100.00 | 100.00 |

TABLE 2

| Classification | | Top discharge stream of decomposition apparatus |
|---|---|---|
| Phenol | (wt %) | 17.03 |
| Alpha-methyl styrene | (wt %) | 65.74 |
| Cumene | (wt %) | 12.69 |
| Acetophenone | (wt %) | 0.06 |
| Etc. | (wt %) | 4.48 |
| Total | (wt %) | 100.00 |

Example 2

As the process flow diagram illustrated in FIG. 1, a phenolic by-product stream of the same compositions as those of Example 1 was fed to a decomposition apparatus 100 at a flow rate of 1,000 kg/hr and the phenolic by-product stream was thermally cracked. In this case, an operation pressure of the decomposition apparatus 100 was controlled to normal pressure and an operation temperature of the decomposition apparatus 100 was controlled to 300° C. Active ingredients of compositions shown in Table 4 were recovered from a top discharge stream of the decomposition apparatus 100. A part of a bottom discharge stream of the decomposition apparatus 100 was fed to a reboiler 200 and a residual stream was discharged. In this case, a side discharge stream of the decomposition apparatus 100 was fed to the reboiler 200 at a flow rate of 300 kg/hr to remove a contaminant accumulated in the reboiler 200 (solid line). Compositions of the side discharge stream of the decomposition apparatus 100 are shown in Table 3.

TABLE 3

| Classification | | Side discharge stream of decomposition apparatus |
|---|---|---|
| Phenol | (wt %) | 29.23 |
| Alpha-methyl styrene | (wt %) | 8.30 |
| Cumene | (wt %) | 1.21 |
| Acetophenone | (wt %) | 61.24 |
| Etc. | (wt %) | 0.02 |
| Total | (wt %) | 100.00 |

TABLE 4

| Classification | | Top discharge stream of decomposition apparatus |
|---|---|---|
| Phenol | (wt %) | 16.83 |
| Alpha-methyl styrene | (wt %) | 63.59 |
| Cumene | (wt %) | 14.61 |
| Acetophenone | (wt %) | 0.04 |
| Etc. | (wt %) | 4.93 |
| Total | (wt %) | 100.00 |

COMPARATIVE EXAMPLES

Comparative Example 1

Figure 2:
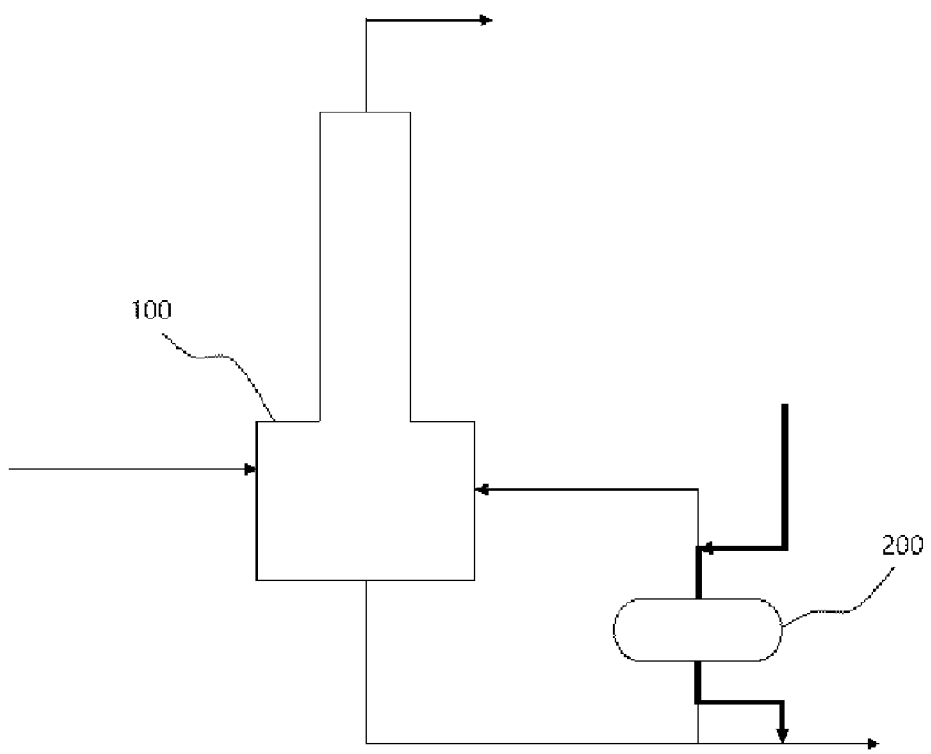
FIG. 2 is a process flow diagram of a method for decomposing a phenolic by-product according to a comparative example.

A phenolic by-product was decomposed in the same manner as that of Example 1 according to a process flow diagram illustrated in FIG. 2, except that acetone (LG Chem Ltd., ACETONE) was fed to a reboiler 200 as a separate cleaning substance (solid line), instead of feeding the side discharge stream of the decomposition apparatus 100 to the reboiler 200.

Comparative Example 2

A phenolic by-product was decomposed in the same manner as that of Example 1 according to the process flow diagram illustrated in FIG. 2, except that a stream of a composition shown in Table 5 which was an organic layer of an acetone product column (APC) BTM separator was fed to the reboiler 200 as a separate cleaning substance (solid line), instead of feeding the side discharge stream of the decomposition apparatus 100 to the reboiler 200.

TABLE 5

| Classification | | Organic layer of APC BTM separator |
|---|---|---|
| Alpha-methyl styrene | (wt %) | 20.00 |
| Cumene | (wt %) | 80.00 |
| Total | (wt %) | 100.00 |

Experimental Example

Figure 3:
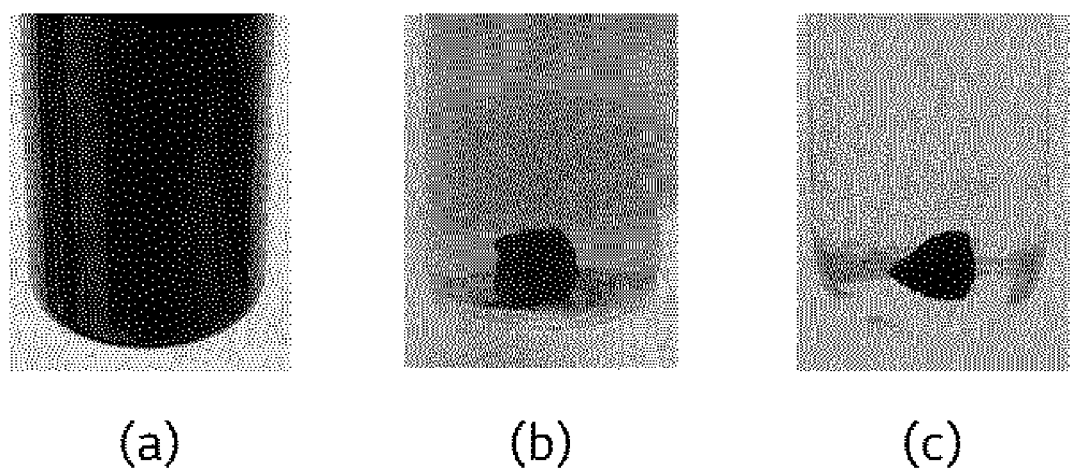
FIG. 3 illustrates photographs showing results of an experiment.

As a contaminant accumulated in the reboiler 200, 5 g of tar having a high boiling point was dipped each of a container in which 50 g of the side discharge stream of Example 1 was contained, a container in which 50 g of the acetone of Comparative Example 1 was contained, and a container in which 50 g of the organic layer component of the APC BTM separator was contained, and each container was left for 7 hours, and solubility of the tar in each container was observed. The results are illustrated in FIG. 3. Specifically, a photograph showing a state where 5 g of tar was dipped in a container in which 50 g of the side discharge stream of Example 1 was contained and the container was left for 7 hours was illustrated in (a) of FIG. 3, a photograph showing a state where 5 g of tar was dipped in a container in which 50 g of the acetone of Comparative Example 1 was contained and the container was left for 7 hours was illustrated in (b) of FIG. 3, and a photograph showing a state where 5 g of tar was dipped in a container in which 50 g of the organic layer component of the APC BTM separator of Comparative Example 2 was contained and the container was left for 7 hours was illustrated in (c) of FIG. 3.

Referring to (a) of FIG. 3, it could be confirmed that in a case where the tar accumulated in the reboiler 200 was dissolved with the side discharge stream of the decomposition apparatus 100 according to the method for decomposing a phenolic by-product, 90% of the tar was dissolved.

In comparison, referring to (b) of FIG. 3, it could be confirmed that in a case where the tar accumulated in the reboiler 200 was dissolved with the acetone, the solubility of the tar was less than 1%, which means that the tar was hardly dissolved. Referring to (c) of FIG. 3, it could be confirmed that in a case where the tar accumulated in the reboiler 200 was dissolved with the organic layer component of the APC BTM separator, the solubility of the tar was less than 1%, which means that the tar was difficult to be dissolved.

It could be appreciated from the facts that in a case where the phenolic by-product was decomposed according to the method for decomposing a phenolic by-product according to the present invention, the tar accumulated in the reboiler 200 was easily dissolved and removed, and it did not require a lot of time to clean the reboiler 200, which was excellent in cost-effectiveness.

The invention claimed is:

1. A method for decomposing a phenolic by-product, the method comprising:
   a step S10 of feeding a phenolic by-product stream to a decomposition apparatus and thermally cracking the phenolic by-product stream;
   a step S20 of recovering an active ingredient from a top discharge stream of the decomposition apparatus and discharging a substance having a high boiling point through a bottom discharge stream of the decomposition apparatus;
   a step S30 of passing a part of the bottom discharge stream of the decomposition apparatus through a reboiler and then feeding the part of the bottom discharge stream of the decomposition apparatus to the decomposition apparatus and discharging a residual stream of the bottom discharge stream of the decomposition apparatus; and
   a step S40 of feeding a side discharge stream of the decomposition apparatus to the reboiler.

2. The method of claim 1, wherein the phenolic by-product is produced from phenol production process.

3. The method of claim 1, wherein the phenolic by-product stream includes one or more selected from the group consisting of phenol, alpha-methyl styrene, acetophenone, cumylphenol, and alpha-methyl styrene dimer.

4. The method of claim 1, wherein the side discharge stream of the decomposition apparatus includes one or more selected from the group consisting of phenol, acetophenone, alpha-methyl styrene, and cumene.

5. The method of claim 1, wherein the side discharge stream of the decomposition apparatus comprises acetophenone in an amount of 50 wt % or more.

6. The method of claim 1, wherein an operation pressure of the decomposition apparatus is 0.1 bar to 3.0 bar.

7. The method of claim 1, wherein a temperature of the side discharge stream of the decomposition apparatus is 150° C. to 500° C.

8. The method of claim 1, wherein a flow rate ratio of the side discharge stream of the decomposition apparatus fed to the reboiler to a flow rate of the phenolic by-product stream is 0.05 to 0.6.

9. The method of claim 1, wherein the step S40 is performed in a state where a connection between the bottom discharge stream of the decomposition apparatus and the reboiler is blocked.

10. The method of claim 1, wherein the top discharge stream of the decomposition apparatus includes one or more selected from the group consisting of phenol, alpha-methyl styrene, and cumene.

* * * * *

UNITED STATES PATENT AND TRADEMARK OFFICE
CERTIFICATE OF CORRECTION

Page 1 of 1

PATENT NO. : 11,414,364 B2
APPLICATION NO. : 17/422686
DATED : August 16, 2022
INVENTOR(S) : Min Suk Kang It is certified that error appears in the above-identified patent and that said Letters Patent is hereby corrected as shown below:

On the Title Page

(73) Assignee: LG Chern, Ltd., Seoul (KR)
Should read as below:
(73) Assignee: LG Chem, Ltd., Seoul (KR)

Signed and Sealed this
Twenty-fifth Day of October, 2022

Katherine Kelly Vidal
*Director of the United States Patent and Trademark Office*